United States Patent [19]

Marsili et al.

[11] 4,124,586

[45] Nov. 7, 1978

[54] RIFAMYCIN COMPOUNDS

[75] Inventors: Leonardo Marsili; Vittorio Rossetti; Carmine Pasqualucci, all of Milan, Italy

[73] Assignee: Archifar Laboratori Chimico Farmacologici S.p.A., Rovereto, Italy

[21] Appl. No.: 738,358

[22] Filed: Nov. 3, 1976

[30] Foreign Application Priority Data

Nov. 12, 1975 [IT] Italy .................................. 5240 A/75

[51] Int. Cl.$^2$ ........................................... C07D 498/18
[52] U.S. Cl. .......................... 260/239.3 P; 424/273 R
[58] Field of Search ................................. 260/239.3 P

[56] References Cited

PUBLICATIONS

Kump et al., "Helv. Chim. Acta", vol. 56, No. 7 (1973) pp. 2348–2377.

*Primary Examiner*—Natalie Trousof
*Assistant Examiner*—Robert T. Bond
*Attorney, Agent, or Firm*—Max Fogiel

[57] ABSTRACT

Novel rifamycin compounds having high antibiotic activity. Such compounds are obtained by reacting 3-amino-rifamycin SV with an aldehyde, particularly an aliphatic or cycloaliphatic aldehyde.

2 Claims, No Drawings

RIFAMYCIN COMPOUNDS

This invention relates to novel Rifamycin compounds having high antibiotic activity.

In DOS patent application No. 2.548.148 in the name of the present applicants, a method has been disclosed for providing 3-amino Rifamycin S having the following formula:

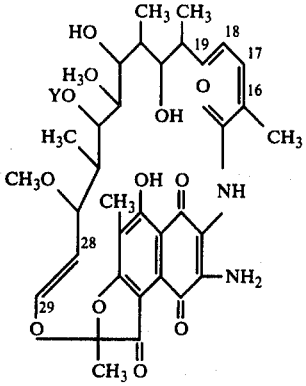
(III)

wherein Y is —COCH$_3$, and its 16, 17, 18, 19 tetrahydroderivative and 16, 17, 18, 19, 28, 29 hexahydroderivative: such compounds show antibiotic characteristics.

Said compounds have been claimed in German Pat. No. 1.670.377.

It is well known that respective 16, 17, 18, 19 tetrahydroderivatives and 16, 17, 18, 19, 28, 29 hexahydroderivatives can be obtained from the rifamycin compounds, such derivatives having comparable characteristics to those of the compounds from which they are derived: the method for obtaining such derivatives would be obvious to those skilled in the art and, for example, is described in the above mentioned German Pat. No. 1.670.377 and in Experientia 20, 336, (1964).

The compounds according to the present invention have the following formula:

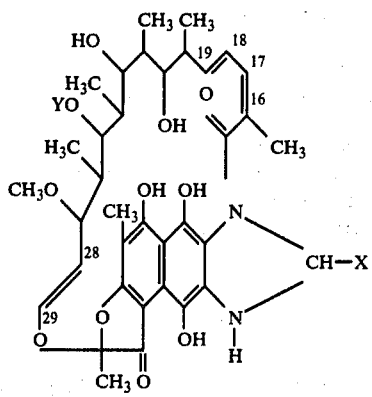
(I)

wherein X is a radical comprising hydrogen; alkyl having less than 14 atoms C; cycloalkyl having less than 7 atoms C in the ring; alkenyl having less than 6 atoms C; cycloalkenyl having less than 7 atoms C in the ring; aryl having less than 13 atoms C; arylalkyl having less than 14 atoms C; arylalkenyl having less than 11 atoms C; a 5 and 6 member heterocycle having 1 atom N; substitution products for the above specified radicals having at least one radical from the group comprising halogen, hydroxyl, alkoxyl, carboxyl, carbalcoxy, carboxyalkoxy, acyloxy, acetamido; Y is —H or —COCH$_3$; and its 16, 17, 18, 19 tetrahydroderivatives and 16, 17, 18, 19, 28, 29 hexahydroderivatives and corresponding oxidized products having the formula

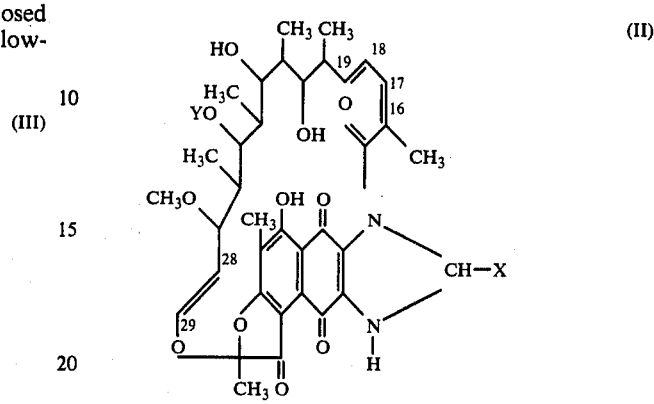
(II)

wherein X and Y are those as defined for formula (I) and also relates to 16, 17, 18, 18 tetrahydroderivatives and 16, 17, 18, 19, 28, 29 hexahydroderivatives either for compounds of formula (I) or those of formula (II).

Products of a similar structure are disclosed in Helvetica Chimica Acta 56, p. 2360-62 and p. 2375-77 (1973). However, such products differ from those of formula I and II by having the N atom at position 3 substituted for by an alkyl rather than by H. These products are obtained by ultraviolet radiation of 3-dialkylamino-rifamycins S, and accordingly such a method is unsuitable for obtaining the compounds of formula I and II. It is well known to those skilled in the art that by reducing rifamycin S and its derivatives substituted at position 3, such as 3-amino-rifamycin S of formula III, the corresponding rifamycins SV are obtained.

The compounds of formula (I) according to the present invention can be obtained by reaction of an aldehyde of formula

wherein X is as above defined, with 3-amino-rifamycin SV.

Similarly, from 16, 17, 18, 19 tetrahydroderivatives and 16, 17, 18, 19, 28, 29 hexahydroderivatives, still by reaction of an aldehyde of the above outlined character, the 16, 17, 18, 19 tetrahydroderivatives and 16, 17, 18, 19, 28, 29 hexahydroderivatives of the compounds of formula (I) are obtained.

By the above mentioned process, depending on the reaction conditions, in addition to the compounds according to the present invention, also compounds can be obtained such as those of a different structure that are the subject of a copending patent application in the name of the present applicants.

Obviously, to obtain the compound of formula (I), 3-amino-rifamycin SV or its desacetylderivative can be directly used as starting product, in which case it would be sufficient to carry out the reaction with the aldehyde; but in practice this procedure would not be convenient because of such a product being readily air oxidable.

All of the compounds of formula (I) according to the present invention are coloured from yellow to orange and have a very high antibiotic activity on gram-positive germs, gram-negative germs and Mycobacterium Tuberculosis.

In order that the present invention be more clearly understood, some unrestrictive exemplary embodiments of the invention will now be described.

EXAMPLE 1

8 g 3-amino-rifamycin S were dissolved in 15 ml tetrahydrofuran, then adding thereto 50 ml acetic acid, 2 g sodium ascorbate and 10 g 2,6-dichlorobenzaldehyde. The solution was stirred at room temperature for 4 hours, 200 ml dichloromethane were added, the mixture was washed with water, then with a saturated acqueous solution of sodium metobisulphite, and finally again with water. The organic phase was dried on sodium sulphate, the solvent was evaporated and the residue recrystallized from ethyl acetate. The process yields 3.5 g of a crystalline product having an orange color, the microanalysis of which exactly agreed with the empirical formula $C_{44}H_{50}Cl_2N_2O_{12}$ corresponding to formula (I), wherein X is 2,6-dichlorophenyl and Y is —$COCH_3$. The electronic spectrum in methanol shows a peak absorption at 460 m$\mu$ ($E_1\%_{cm} = 100$).

The nuclear magnetic resonance spectrum in deuterochloroform, by using tetramethylsilane as internal reference, shows the most significant peaks at $\delta$: 13.68 (s); 12.14 (s); 11.23 (s); 7.58/7.12 (m); 6.45/5.90 (m); 5.35/4.95 (m); 4.74/4.60 (m); 4.10/3.48 (m); 3.10/2.18 (s); 2.08 (s); 1.77 (s); 1.28 (s); 1.22/0.60 (m) and 0.17/—0.11 (m) p.p.m.

EXAMPLE 2

8 g 3-amino-rifamycin S were dissolved in 10 ml methanol and 40 ml tetrahydrofuran. 2 g ascorbic acid and 5.6 g 2-chlorobenzaldehyde were added.

The solution was stirred at room temperature for one night, the solid product obtained was filtered and the precipitate washed with a few millilitres of a 4:1 mixture of tetrahydrofuran and methanol. The product was dissolved in 200 ml chloroform, washed with a saturated aqueous solution of sodium metabisulphite and then with water. After drying on sodium sulphate, the solvent was evaporated and the residue was suspended in petroleum ether. The suspension was filtered to obtain 4.3 g of an orange colour product of formula I, wherein X is 2-chlorophenyl and Y is —$COCH_3$. The electronic absorption spectrum in methanol shows a peak at 455 m$\mu$ ($E_{1cm}^{1\%} = 119$).

EXAMPLE 3

8 g 3-amino-rifamycin S were dissolved in 30 ml tetrahydrofuran and 10 ml methanol. The solution was added with 2 g ascorbic acid, 5 ml propionic aldehyde and 10 ml acetic acid. After 3 hours stirring at room temperature, 250 ml benzene were added, the mixture was washed with water, then with an aqueous solution of bisodic phosphate and then again with water. The organic phase, as dried o, sodium sulphate, was dry evaporated and the residue several times recrystallized from methyl alcohol. 2.8 g of a product of formula I were obtained, wherein X is ethyl and Y is —$COCH_3$.

The electronic absorption spectrum in methanol shows a peak at 465 m$\mu$ ($E_{1cm}^{1\%} = 123$).

EXAMPLE 4

8 g 3-amino-rifamycin S were dissolved in 25 ml diglyme and then reduced with a solution of 2 g sodium ascorbate in 6 ml water. The solution was stirred at room temperature for 5 minutes and added with 3.5 ml cyclohexancarboxyaldehyde. After further 10 minutes, 25 ml chloroform were added. After further stirring at room temperature for 60 minutes, the solution was diluted with 30 ml chloroform, once washed with water, added with 150 ml ethyl ether, washed again with water containing sodium ascorbate, and then with only water. The organic phase was dried on sodium sulphate, the solution was half concentrated and allowed to crystallize. By filtering, 5.2 g of an orange color product of formula I were obtained, wherein X is cyclohexyl and Y is —$COCH_3$.

The electronic absorption spectrum in methanol shows a peak at 455 m$\mu$ ($E_{1cm}^{1\%} = 124.5$). The nuclear magnetic resonance spectrum in $CDCl_3$, using tetramethylsilane as internal reference, shows the most significant peaks at $\delta$: 13.90 (s); 12.35 (s); 11.50 (s); 5.15 (dd); 5.01 (d); 3.07 (s); 2.17 (s); 2.08 (s); 1.75 (s); 1.3/1.9 (m); 1.03 (d); 0.88 (d); 0.75 (d) and —0.08 (d) p.p.m.

EXAMPLE 5

8 g 3-amino-rifamycin S were dissolved in 40 ml tetrahydrofuran, added with 1.5 g ascorbic acid and 0.5 g sodium ascorbate. 10 ml methyl alcohol and then 4 g 4-chlorobenzaldehyde were added.

Following one night stirring at room temperature, the precipitate obtained was filtered, dissolved in 200 ml chloroform, and the solution was washed with water, an aqueous solution of sodium metabisulphite and then again with water.

The organic phase was dried on sodium sulphate and then dry evaporated. The residue was suspended in petroleum ether and the suspension filtered to yield 1.5 g of an orange colour product of formula I, wherein X is 4-chlorophenyl and Y is —$COCH_3$. The electronic absorption spectrum in methanol shows a peak at 455 m$\mu$ ($E_{1cm}^{1\%} = 120$).

EXAMPLE 6

8 g 3-amino-rifamycin S were dissolved in 20 ml tetrahydrofuran, reduced with 1.5 g ascorbic acid and 0.5 sodium ascorbate and then reacted with 5 g 2-carboxybenzaldehyde dissolved in 20 ml tetrahydrofuran and 10 ml methyl alcohol. The solution was stirred at room temperature for 2 hours and poured into a solution of 15 g sodium sulphite in 600 ml water. The reaction mixture was added with 15 ml acetic acid, filtered, washed with water and dried. The solid product was extracted with ethyl ether and by evaporation of the solvent 1.2 g were obtained of a product of formula I, wherein X is 2-carboxyphenyl and Y is —$COCH_3$.

The electronic absorption spectrum in methanol shows a peak at 450 m$\mu$ ($E_{1cm}^{1\%} = 97$).

EXAMPLE 7

8 g 3-amino-rifamycin S were dissolved in 40 ml tetrahydrofuran, addded with 5 g 2-pyridincarbaldehyde, and then with 1.5 g ascorbic acid, 10 ml methyl alcohol and 0.5 g sodium ascorbate.

The solution was stirred at room temperature for 60 minutes, added with 200 ml benzene, washed with an aqueous solution of bisodic phosphate, an aqueous solution of sodium metabisulphite and finally with water only. The resulting solution was dried on sodium sulphate, concentrated to a small volume, diluted with petroleum ether to obtain 6 g of a product of formula I, wherein X is 2-pyridyl and Y is —$COCH_3$.

The electronic absorption spectrum in methanol shows a peak at 455 mμ ($E_{1cm}^{1\%} = 111$).

EXAMPLE 8

1 g of the product obtained in Example 1 was dissolved in 30 ml chloroform and 5 ml methanol. The solution was added with 0.5 g manganese dioxide and stirred at room temperature for 30 minutes. The product was filtered and the solvent evaporated to obtain 0.8 g of a green color product of formula II, wherein X is 2,6-dichlorophenyl and Y is —COCH$_3$.

The electronic absorption spectrum in methanol shows absorption peaks at 630 mμ, 400 mμ (sp), 330 mμ (sp) and 266 mμ ($E_{1cm}^{1\%} = 281.8$).

EXAMPLE 9

8 g 3-amino-rifamycin S dissolved in 25 ml diglyme were reduced with a solution of 2 g sodium ascorbate in 6 ml water. After adding 3.5 ml 2-ethylbutanal, the solution was stirred at room temperature for 10 minutes, diluted with 25 ml chloroform and stirred for further 60 minutes. The reaction mixture was washed with water, the organic phase dried and evaporated to obtain an oily residue. By extracting with petroleum ether, a solution was obtained which concentrated and allowed to crystallize in refrigerator yielded after filtration 2.7 g of a product of formula I, wherein X is 3-penthyl and Y is —COCH$_3$.

The electronic absorption spectrum in methanol shows peaks at 462 mμ ($E_{1cm}^{1\%} = 123$). By using 25-desacetyl-3-amino-rifamycin S, a product of formula I is obtained, wherein X is 3-penthyl and Y is —H, and the electronic absorption spectrum in methanol of which shows the same peak at 462 mμ ($E_{1cm}^{1\%} = 130$).

EXAMPLE 10

8 g 3-amino-rifamycin S were dissolved in a mixture of 25 ml acetic acid and 15 ml tetrahydrofuran. The solution was added with 1 g zinc, 4 ml 3-phenylpropionaldehyde and stirred at room temperature for 30 minutes. The reaction mixture was dropwise poured into a solution of 20 g sodium sulphite and 5 g sodium ascorbate in 600 ml water and filtered again, the precipitate was washed with water and dried in a stove at 40° C. 7.3 g of a product of formula I were obtained, wherein X is β-phenethyl and Y is —COCH$_3$. The electronic absorption spectrum in methanol shows a peak at 460 mμ ($E_{1cm}^{1\%} = 100$). Similarly, by reacting 3-amino-16, 17, 18, 19, 28, 29-hexahydro-25-desacetyl-rifamycin S, the 25-desacetyl-16, 17, 18, 19, 28, 29-hexahydroderivative of the product characterized in the above disclosed example will be provided.

EXAMPLE 11

8 g 3-amino-rifamycin S were dissolved in a mixture of 25 ml acetic acid and 15 ml tetrahydrofuran. The solution was then added with 1 g zinc and 2.5 g 3-methylcrotonaldehyde. After stirring at room temperature for 30 minutes, the reaction mixture was filtered and dropwise poured into 400 ml ethyl ether. This product was filtered again and the ether phase was washed with phosphate buffer at pH 7.5 and then with water. After drying and solvent evaporation, the residue was extracted with petroleum ether and the solution obtained was evaporated to obtain 1.3 g of a product of formula I, wherein X is 2-methylpropyl-1-ene and Y is —COCH$_3$.

The electronic absorption spectrum in methanol shows a peak at 453.5 mμ ($E_{1cm}^{1\%} = 114.3$).

EXAMPLE 12

8 g 3-amino-rifamycin S were dissolved in 30 ml diglyme and the solution was then added with 2 g sodium ascorbate dissolved in 5 ml water. The solution of 3-amino-rifamycin SV thus obtained was heated to 50° C. and then added with 4.4 g 4-carboxybenzoic aldehyde. The solution was stirred at this temperature for 15 minutes and then after adding 30 ml chloroform was again stirred at 50° C. for 4 hours. The reaction mixture was then added with 300 ml chloroform, washed with an aqueous solution of sodium metabisulphite and then with water.

After drying and chloroform evaporation, the solid product was extracted with 500 ml ethyl ether, the ether phase was washed with phosphate buffer at pH 7.5 and then with water only. The product was dried, concentrated to 30 ml, added with 50 ml petroleum ether and allowed to crystallize. 1.7 g of a product of formula I were obtained, wherein X is 4-carboxyphenyl and Y is —COCH$_3$.

The electronic absorption spectrum in methyl alcohol shows a peak at 449.5 mμ ($E_{1cm}^{1\%} = 58$).

EXAMPLE 13

8 g 3-amino-rifamycin S were dissolved in a mixture of 25 ml acetic acid and 15 ml tetrahydrofuran. The solution was added with 1 g zinc and 4.3 g 3-carbetoxycyclohexancarboxaldehyde and stirred at 15° C. for 30 minutes. The reaction mixture was filtered and dropwise poured into a solution of 15 g sodium sulphite in 500 ml water. The precipitate thus formed was filtered, washed and dried. The product was dissolved again in 50 ml methyl alcohol, adding 1 g ascorbic acid and after stirring for 10 minutes diluted with 300 ml ethyl ether. The resulting solution was washed with phosphate buffer at pH 7.5, then with water and after drying ethyl ether was evaporated. The residue obtained was suspended in 500 ml petroleum ether and maintained under stirring for 30 minutes. Following filtering and drying in a stove at 40° C., 6 g of a product of formula I were obtained, wherein X is 3-carbethoxycyclohexyl and Y is —COCH$_3$.

The electronic absorption spectrum in methanol shows a peak at 455 mμ ($E_{1cm}^{1\%} = 97.2$).

EXAMPLE 14

8 g 3-amino-rifamycin S were dissolved in 25 ml diglyme and added with a solution of 2 g sodium ascorbate in 5 ml water and 3.5 ml 3-cyclohexencarboxyl aldehyde. After stirring for 10 minutes, 25 ml chloroform were added and stirring was continued at room temperature for 3 hours. The reaction mixture was diluted with 200 ml chloroform, washed with an aqueous solution of sodium metabisulphite and then with water. After drying on sodium sulphate, the mixture was concentrated to 50 ml and diluted with 150 ml petroleum ether. The precipitate was filtered and 1.8 g of a product of formula I, wherein X is 3-cyclohexene and Y is —COCH$_3$, crystallized from the solution left for one night in a refrigerator.

The electronic absorption spectrum in methanol shows a peak at 460 mμ ($E_{1cm}^{1\%} = 119$). Similarly, by reacting 3-amino-16, 17, 18, 19, 28, 29-hexahydro-25-desacetyl-rifamycin S, the 25-desacetyl-16, 17, 18, 19, 28, 29-hexahydroderivative of the product characterized in the above disclosed example will be provided.

EXAMPLE 15

8 g 3-amino-rifamycin S were dissolved in a mixture of 15 ml tetrahydrofuran, 25 ml acetic acid and 2.2 g 2-methoxyacetaldehyde. After addition of 1 g zinc, the solution was stirred at room temperature for 60 minutes, filtered and dropwise poured into a solution of 15 g sodium sulphite in 600 ml water. The solid product formed was filtered, washed with water and dried. The resulting product was crystallized from methanol to obtain 4.7 g of a product of formula I, wherein X is methoxymethyl, Y is —COCH$_3$ and of which the electronic absorption spectrum in methanol shows a peak at 450 m$\mu$ ($E_{1cm}^{1\%}$ = 125).

EXAMPLE 16

16 g 3-amino-rifamycin S were dissolved in 60 ml diglyme and the solution was added with 4 g sodium ascorbate dissolved in 10 ml water. After stirring at room temperature for 10 minutes, 9 g 2-fluoro-6-chlorobenzoic aldehyde and 60 ml chloroform were added. The reaction mixture was stirred again at 50° C. for 2 hours. The solid precipitate was filtered, washed with chloroform and dissolved again in 100 ml methyl alcohol. The solution was filtered, concentrated to 60 ml and allowed to crystallize for one night in a refrigerator. The resulting product was filtered to obtain 3.8 g of a crystalline product. From the concentrated mother liquors, further 2.5 g are obtained of a product identical to the former of formula I, wherein X is 2-fluoro-6-chlorophenyl.

The electronic absorption spectrum in methanol shows a peak at 458 m$\mu$ ($E_{1cm}^{1\%}$ = 132.9).

The nuclear magnetic resonance spectrum in CDCl$_3$/DMSO-d$_6$, by using tetramethylsilane as internal reference, shows the most significant peaks at $\delta$: 18.02(s); 14.27(s); 12.21(s); 7.0/7.4(m); 6.93(s); 5.10(d); 5.06(dd); 3.02(s); 2.14(s); 2.05(s); 1.73(s); 1.28(s); 1.04(d); 0.94(d); 0.75(d) and −0.11(d) p.p.m.

By the process described in this example, in addition to the above defined compound, chromatography on thin layer has pointed out the formation of a different compound which is the subject of a copending patent application in the name of the present applicants.

EXAMPLE 17

8 g 3-amino-rifamycin S were dissolved in 15 ml tetrahydrofuran and added at room temperature with 25 ml acetic acid, 5 g undecanal and 1 g zinc. After stirring for 30 minutes, the undissolved zinc was filtered and the filtrate dropwise added to a solution of 30 g sodium sulphite in 700 ml water. The solid material separated, several times washed with water, was then stirred for 30 minutes with 200 ml petroleum ether. The suspension was filtered and the solid product obtained was dried at 40° C., to obtain 5.6 g of a product of formula I, wherein X is n-decyl and Y is —COCH$_3$.

The electronic absorption spectrum in methanol shows a peak at 456 m$\mu$ ($E_{1cm}^{1\%}$ = 107.8).

EXAMPLE 18

8 g 3-amino-rifamycin S were dissolved in a mixture of 50 ml acetic acid and 15 ml tetrahydofuran. The solution was then added with 1.5 g zinc and 7.6 g 2-dimethyl-1-hydroxypropan-1- sodium sulphonate. After stirring at room temperature for 40 minutes, the suspension was filtered, the filtrate was dropwise added to a solution of 15 g sodium sulphite in 500 ml water, and this solution was filtered again, washed with water and dried at 40° C. The raw product was stirred for 30 minutes with 500 ml ethyl ether, the ether solution was washed with phosphate buffer at pH 7.5, then washed with water and finally after anhydrification concentrated to 50 ml. After dilution with 100 ml petroleum ether, the product was left in a refrigerator for one night, filtered and the solvent was evaporated to obtain 1.5 g of a product of formula I, wherein X is t-butyl and Y is —COCH$_3$.

The electronic absorption spectrum in methyl alcohol shows a peak at 455 m$\mu$ ($E_{1cm}^{1\%}$ = 61.8).

What we claim is:

1. A rifamycin compound having the formula

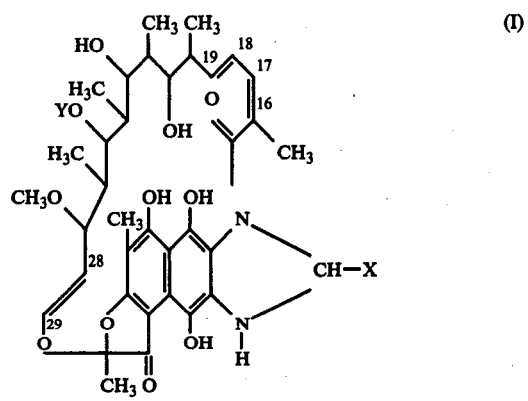

wherein: X is a radical selected from the group comprising hydrogen; alkyl having from 1 to 13 C atoms; cycloalkyl having from 3 to 6 C atoms in the ring; alkenyl having from 2 to 5 C atoms; cycloalkenyl having from 5 to 6 C atoms in the ring; aromatic hydrocarbon having from 6 to 12 C atoms; aromatic hydrocarbon-alkyl having from 7 to 13 C atoms; aromatic hydrocarbon-alkenyl having from 8 to 10 C atoms; a 5 and 6 member heterocycle having only 1 heteroatom consisting of an atom N; substitution products of the above specified radicals having from 1 to 4 radicals selected from the group consisting of halogen, hydroxyl, alkoxyl, carboxyl, carboalkoxy, carboxyalkoxy alkanoyloxy, acetamido; Y is —H or —COCH$_3$; and its 16, 17, 18, 19 tetrahydroderivatives and 16, 17, 18, 19, 28, 29 hexahydroderivatives and corresponding oxidized products having the formula

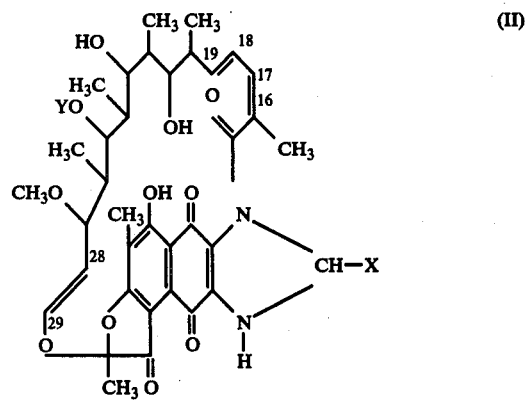

wherein X and Y are those as defined for formula (I) and also relates to 16, 17, 18, 19 tetrahydroderivatives and 16, 17, 18, 19, 28, 29 hexahydroderivatives for the compounds of formula (II).

2. A process for producing rifamycin compounds of formula (I) according to claim 1, wherein an aldehyde having the formula

X — CHO wherein X is as defined in claim 3 is reacted with 3-amino-rifamycin SV in an organic solvent selected from the group comprising alcohols and chlorinated solvents having from 1 to 5 C atoms and ethers having from 4 to 8 C atoms, at a temperature ranging from 10° C. 70° C. for a time between a few minutes and 24 hours.

* * * * *